United States Patent
Rovison et al.

(10) Patent No.: US 9,351,488 B2
(45) Date of Patent: *May 31, 2016

(54) PERACETIC ACID COMPOSITION

(75) Inventors: John M. Rovison, Sanborn, NY (US);
Donald Lapham, Lockport, NY (US);
Shibu Abraham, Stewartsville, NJ (US);
Mary Homan, San Antonio, TX (US)

(73) Assignee: PEROXYCHEM LLC, Philadelphia, PA (US)

(*) Notice: Subject to any disclaimer, the term of this patent is extended or adjusted under 35 U.S.C. 154(b) by 1832 days.

This patent is subject to a terminal disclaimer.

(21) Appl. No.: 12/519,889

(22) PCT Filed: Dec. 20, 2007

(86) PCT No.: PCT/US2007/088409
§ 371 (c)(1),
(2), (4) Date: Jun. 18, 2009

(87) PCT Pub. No.: WO2008/079999
PCT Pub. Date: Jul. 3, 2008

(65) Prior Publication Data
US 2009/0312292 A1    Dec. 17, 2009

Related U.S. Application Data

(60) Provisional application No. 60/876,941, filed on Dec. 22, 2006.

(51) Int. Cl.
| | | |
|---|---|---|
| *A01N 37/40* | (2006.01) | |
| *A01N 37/16* | (2006.01) | |
| *A01N 37/36* | (2006.01) | |
| *A23B 4/12* | (2006.01) | |
| *A23B 7/10* | (2006.01) | |
| *A23C 7/02* | (2006.01) | |
| *A23L 3/349* | (2006.01) | |
| *A23L 3/3508* | (2006.01) | |

(52) U.S. Cl.
CPC ............... *A01N 37/40* (2013.01); *A01N 37/16* (2013.01); *A01N 37/36* (2013.01); *A23B 4/12* (2013.01); *A23B 7/10* (2013.01); *A23C 7/02* (2013.01); *A23L 3/349* (2013.01); *A23L 3/3508* (2013.01)

(58) Field of Classification Search
CPC ....... A01N 37/40; A01N 37/16; A01N 37/36; A01N 2300/00; A23B 4/12; A23B 7/10; A23C 7/02; A23L 3/349; A23L 3/3508
See application file for complete search history.

(56) References Cited

U.S. PATENT DOCUMENTS

| | | | |
|---|---|---|---|
| 4,051,058 A | 9/1977 | Bowing et al. | |
| 4,775,424 A | 10/1988 | Wisotzki et al. | |
| 5,116,575 A | 5/1992 | Badertscher et al. | |
| 5,407,685 A | 4/1995 | Malchesky et al. | |
| 6,387,238 B1 | 5/2002 | Merk et al. | |
| 6,475,967 B1 | 11/2002 | Arvanitidou et al. | |
| 6,617,290 B2 | 9/2003 | Lopes | |
| 6,767,569 B1 | 7/2004 | Marsden et al. | |
| 6,828,294 B2 * | 12/2004 | Kellar et al. | 510/382 |
| 7,691,630 B2 * | 4/2010 | Moon et al. | 435/420 |

FOREIGN PATENT DOCUMENTS

| | | |
|---|---|---|
| EP | 0395296 A2 | 10/1990 |
| EP | 0720814 A1 | 7/1996 |

OTHER PUBLICATIONS

Extended European Search Report and Opinion, Dated Jun. 14, 2013, Application No. 07871725.3-1358/2094118 PCT/US2007088409.

* cited by examiner

*Primary Examiner* — Kendra D Carter
(74) *Attorney, Agent, or Firm* — Duane Morris LLP

(57) ABSTRACT

The invention relates to anti-microbial compositions useful against a wide range of microorganisms undesirable on a wide variety of materials, including food, food contact and non-food contact surfaces, and surfaces in industrial, recreational, health care, and other institutional environments. More particularly, the anti-microbial compositions comprise peracetic acid in combination with a) citric acid or a salt and b) salicylic acid or a salt in aqueous solution.

16 Claims, No Drawings

PERACETIC ACID COMPOSITION

CROSS REFERENCE TO RELATED APPLICATION

This application claims the benefit of U.S. Provisional Application No. 60/876,941, filed Dec. 22, 2006.

FIELD OF THE INVENTION

The invention relates to anti-microbial compositions useful against a wide range of microorganisms that are undesirable on a wide variety of materials, including food, food contact and non-food contact surfaces, and surfaces in industrial, recreational, health care, and other institutional environments. More particularly, the anti-microbial compositions comprise an aqueous solution of peracetic acid (PAA) and an adjuvant, the adjuvant comprising a) citric acid or a salt of citric acid and b) salicylic acid or a salt of salicylic acid.

BACKGROUND OF THE INVENTION

Certain environments pose challenges to the efficacy of sanitizers and disinfectants upon various microorganisms found within those environments. Additionally, a number of widely applied antimicrobial control agents have effectively been reduced because of their inherent toxicity, long term and latent effects on the environment, food chain, and surface waters. A number of compounds are undergoing increased scrutiny because of these factors coupled with misapplication and general in-use safety.

Peracetic acid is known to be a useful antimicrobial agent. However, its antimicrobial effect is best obtained with high concentrations (generally greater than 100 parts per million (ppm)). At these concentrations the material has an overbearing odor, sometimes causes oxidative damage to foodstuffs and surfaces to which it is applied, and present hazards to persons handling the materials. U.S. Pat. No. 4,051,058 discloses aqueous solutions of peracetic acid in concentrations of 0.5% to 20% by weight for use in sanitizing and disinfecting applications. Compositions additionally containing organic acids are also known. U.S. Pat. No. 6,617,290 discloses the use of acidifying agents classified as GRAS (Generally Regarded As Safe) for use as food additives in preparations for cleaning and sanitizing food contact and non-food contact surfaces. These agents include citric and lactic acids. U.S. Pat. No. 6,475,967 discloses a light duty antibacterial liquid detergent displaying foaming and grease-cutting as well as low corrosive properties. The aqueous composition comprises hydroxyl-containing organic acid(s), a peracetic acid, and other components including various surfactants, and polyethylene glycol.

A need continues to exist for antimicrobial compositions that are stable, environmentally compatible, are "no rinse" after application, exhibit residual anti-microbial activity, do not alter organoleptic properties such as taste, smell, or visual appearance of food which comes into contact with the composition, will not oxidize hard surfaces, and will not adversely affect humans should incidental ingestion or contact occur. Particularly desirable are antimicrobial compositions that are effective at low concentrations in solution.

SUMMARY OF THE INVENTION

The invention is a cleaning and sanitizing composition comprising, in aqueous solution,
 a. peracetic acid; and
 b. an adjuvant comprising (i) salicylic acid or its salts and (ii) citric acid or its salts.

The invention further includes the adjuvant wherein the salicylic acid and citric acid or their respective salts are dissolved to their solubility limits and in proportionate ratios ranging from about 1:5 to 1:1 by weight respectively. One or more stabilizing agents, wetting agents, hydrotopes, thickeners, foaming agents, acidifiers, pigments, dyes, surfactants, or combinations thereof may further be components of the invention to effect other properties desirable in such a composition. One such surfactant consists of one or more anionic or nonionic surfactants in concentrations up to 2% selected from the group FMC HRS™, polyoxylene ($C_{20}$ to $C_{80}$) sorbitan monooleates, alklyl long chain fatty acid ($C_5$ to $C_{20}$) metallic esters and alcohols; and alkylbenzenesulfonic acids and alcohols and/or their metallic ester salts having alkyl groups ranging from $C_2$ to $C_{20}$.

The invention further includes a kit comprising
 a. an aqueous peracetic acid solution; and
 b. a mixture comprising salicylic acid and citric acid or their respective salts in proportionate ratios ranging from about 1:5 to 1:1 by weight respectively and in a solution matrix acting as solvent of glacial acetic acid (70-90%) and water (30-5%).

The invention also encompasses a method of reducing microbial contamination comprising applying the anti-microbial composition to a surface in an amount and for a time sufficient to reduce the microbial contamination. The surface to which the composition is applied is any of meat, poultry, seafood, or portions thereof. The surface may alternatively be a plant material (leaf, stalk, flower, fruit, vegetable, or portion thereof). Additionally, the surface may be a non-food surface. The method further contemplates recovering the applied composition and reprocessing the recovered composition to yield a recycled anti-microbial composition. The method includes an embodiment wherein the peracetic acid component is present at end use concentrations ranging up to 1%. The invention further contemplates a composition wherein the sodium salicylate or salicylic acid is present at end use at up to 20000 ppm. The invention further contemplates a composition wherein the citric acid is present at end use at up to 20000 ppm. End use concentrations of the composition generally have pH values between 1 and 4.5.

DESCRIPTION OF THE PREFERRED EMBODIMENTS

The present invention relates to improved mycocidal and bacteriocidal compositions that are safe for food contact and non-food surfaces without requiring a post-sanitizing rinse and are safe for incidental human contact. The composition of the invention is intended to enhance the efficacy of peracetic acid solutions at end use concentrations. The invention is a composition comprising:
 a) an aqueous peracetic acid solution; and
 b) an adjuvant comprising (i) salicylic acid or its salts (cationic valence +1 or +2) and (ii) citric acid or its salts (cationic valence +1 or +2).

The aqueous adjuvant solution comprises 70-95% acetic acid and 30-5% by weight water containing the salicylic acid and the citric acid components dissolved in the liquid. The resulting adjuvant is then added to the peracetic acid/water solution such that the upper ppm limit of PAA is about 10,000 ppm and the upper ppm limit of the other acids is about 40,000 ppm. One method of forming the invention includes adding to the peracetic acid formulation in situ salicylic acid or its salts (as a simple form of an aromatic carboxylic acid) and citric acid or its salts (as a tricarboxylic acid). Salicylic acid and citric acid are used to form the adjuvant in concentrations of from about 100 ppm to about 40,000 ppm. Above this concentration the additive formulation itself becomes unstable (acetic acid+water+sodium salicylate+citric acid) to support addition into the PAA/water solution.

The resulting peracetic acid in situ mixture containing the adjuvant provides enhanced performance and latent residual activity on a treated surface once the liquid portions have disappeared through decomposition and evaporation. Additional components may be anionic or non-ionic surfactants which can foam and thereby hold the sanitizer in place for extended periods of time. The composition contains peracetic acid at end use concentrations of between about 40 ppm to about 10,000 ppm. Any lower use concentrations of peracetic acid require too long of a contact time to be considered practicably effective. The final diluted solution as applied to a food stuff or surface will contain by weight in one embodiment approximately water 84.5-91.4%; acetic acid 10.1-0.149%; PAA 1-0.004%; hydrogen peroxide 4-0.003%; citric acid or salt 0.56-0.010%; and, salicylic acid or salycilate salts 0.12-0.002%. All percents here and elsewhere throughout the application are percents by weight unless indicated otherwise.

The compositions of the invention are appropriate for use in food and beverage processing plants (including facilities related to meat, seafood, poultry, produce, dairies, wineries, breweries, and beverage plants), food preparation kitchens, food serving establishments, nursing-care and hospital-care applications, and industrial and institutional surfaces where concerns exist regarding the safety of food products, environmental residues, or for human contact. The composition can be applied either through in situ mixing via batch tank, in-line mixing with ratio controllers or ratio control via pump speeds, or topical application of one liquid separately into/onto one another upon the surface to be treated. The invention is also provided in the form of a kit containing an aqueous peracetic acid solution as a first component and a concentrate of salicylic and citric acid or salts thereof as a second component.

Although not wishing to be bound to any particular theory, the following information is presented to assist those skilled in the art to understand the applicability and limits of this invention.

Yeasts and molds have a typical surface structure containing a cell wall generally comprised of 1,3-α-peptidoglycans and/or chitin along with the lipid bi-layer associated with cell membranes. The slightly different construction of fungal cell walls relative to the 1,4 and 1,6-α-peptidoglycans associated with bacteria having cell walls (gram positive) presents some different characteristics when attempting to destroy the organism.

The intent of the invention is to disrupt the metabolic homeostatic mechanisms of the target organisms with a mixture of antimicrobial compounds. All antimicrobial agents will have some toxic effects to lower and higher forms of life, including animals and humans, because all life forms share some degree of common metabolic pathways. Typical homeostatic metabolic mechanisms include: protein coagulation, lysing, oxidation, reduction, and competitive and non-competitive inhibition. More specifically, citric acid disrupts respiratory pathways via Kreb's cycle and has known preservative properties. Salicylic acid derivatives inhibit folic acid synthesis in mycobacterium and are bacteriostatic. These derivatives are known for their use as preservatives, fungicides (i.e., as a treatment of tinea), and have mild antibiotic properties when used as a topical treatment for skin ailments. These compounds weaken the target organism and so enhance the efficacy of peracetic acid in oxidative lysing.

Cell damage is distinguished as "-static" or "-cidal" activity based on the degree of the control agent's efficacy and defined by official laboratory control protocols. "Static" cell damage is reversible, with the organism able to multiply once relieved of exposure to the agent. "-cidal" cell damage is irreversible, with lethality resulting from complete microbial cell destruction or incapacitation. According to this definition, preservatives are generally considered inhibitory, bacteriostatic, or mycobacteriostatic and sanitizers and disinfectants are considered microbiocidal.

Preservatives are inhibitory compounds added to foods and non-food products to prolong or enhance shelf-life by hindering the deterioration of properties such as: texture, nutritive value, odor, flavor, color, appearance, value or safety. Minimum Inhibitory Concentration is the standard criteria for evaluating such materials as is Zone of Inhibition. The key differentiators between preservatives and sanitizers are: 1) mode of action—preservatives prevent growth instead of demonstrating lethality; and 2) exposure time—preservatives operate over periods of days to months whereas sanitizers must provide 99.9999% (5 log order) lethality within 30 seconds at nominal 20 degrees C.

Sanitizers reduce microbial contaminants to levels deemed safe as given by public health requirements and must result in 99.9999% reduction (5 log order reduction) from a practical perspective for given organisms as defined by Germicidal and Detergent Sanitizing Action of Disinfectants, Official Methods of Analysis of the Association of Official analytical Chemists, paragraph 960.09 and applicable sections, $15^{th}$ Edition, 1990 (EPA Guideline 91-2). Disinfectants must pass a more stringent antimicrobial test; the A.O.A.C. Use Dilution Methods, Official Methods of Analysis of the Association of Official analytical Chemists, paragraph 955.14 and applicable sections, 15th Edition, 1990 (EPA Guideline 91-2).

It is desirable that sanitizing agents or compounds have key properties beyond antimicrobial efficacy. They include "no rinse" after application and exhibit residual activity where "residual activity" refers to some latent antimicrobial effects remain on the treated surface if contaminated by microorganisms during storage or lag periods by means of a lingering coating or film. Additionally, the sanitizer ought not to alter food or (organoleptic properties such as taste, smell, or visual appearance) if food contact occurs and should not affect humans should incidental ingestion result.

Compositions:

The compositions of the present invention comprise (a) peracetic acid (b) salicylic acid or a salt thereof and (c) citric acid or a salt thereof.

Peracetic acid is well known for its highly oxidative properties and as a bactericide and fungicide, especially in food processing operations. VigorOx® Liquid Sanitizer & Disinfectant and VigorOx® LS (LS&D and LS, FMC, USA) are equilibrium mixtures of peracetic acid, hydrogen peroxide, acetic acid, water and stabilizer. They are used at low solution concentrations to rapidly kill a broad spectrum of microorganisms including gram-positive and gram negative bacteria. They are more tolerant than most sanitizers to pH, temperature, water hardness, and organic soils. The products are EPA-registered solutions for the food and beverage industry. VigorOx® LS&D's and VigorOx® LS's no-rinse, non-foaming formulas and their ability to sanitize at cold temperatures make them ideally suited for use in circulation clean-in-place (CIP) systems for food processing equipment. VigorOx® LS&D and VigorOx® LS are also approved for immersion cleaning of equipment and utensils in food processing and packaging plants and eating establishments. VigorOx®

LS&D is composed of: PAA 5-6%; $H_2O_2$ 21-23%; acetic acid 10-11%; and water 63-65%. Clarity®, Blitz®, and Spectrum® are additional FMC formulations of peracetic acid. The compositions for Clarity®, Blitz®, Spectrum®, and VigorOx® SP-15 are identical with registration differences for their intended use: PAA 15-17%; $H_2O_2$ 9-11%; acetic acid 33-38%; sulfuric acid 0-1%; and water 30-44%.

Salicylic acid is well known as the substructure for common aspirin, is easily metabolized at low exposure rates, and is known as a mild antibiotic for skin-care products targeting acne, psoriasis, calluses, corns, keratosis pilaris, and warts. It is also known for inhibiting genes necessary for pathenogensis in some soil microbes, such as *Pseudomonas aeruginosa*.

Citric acid and its salts are well established as preservatives in food, especially beverages, and as pH buffers in solutions. Citric acid is Generally Regarded As Safe (GRAS) by the FDA.

In addition to the free citric or salicylic acids, the compositions of the present invention may alternatively contain "salts" of these acids. The salts may be salicylate salt(s) comprising cationic salts including, but not limited to, sodium, potassium, ammonium; salicylates salts of cations with valences of +1 and +2, or alkyl ($C_2$ to $C_{20}$), or acetyl derivatives and/or with side chains in the ortho, meta, and/or para positions of alkyl, aryl, acetyl, or carboxy side chains of length $C_2$ to $C_{20}$. Salts may also be citric acid ester salts of cations with valences of +1 and +2 including complex cations such as ammonium. A preferred composition comprises peracetic acid, sodium salicylate and citric acid.

The compositions of the present invention upon drying will leave minute amounts of salicylic acid or its salts and citric acid or its salts after the peracetic acid has decomposed or has been lost by evaporation. This effect will provide for some extended latent antimicrobial effects.

Additives:

The compositions may further comprise a variety of other optional ingredients such as surfactants, wetting agents, hydrotopes, thickeners, foaming agents, acidifiers, builders, stabilizers, bleach activators, soil suspenders, dye transfer agents, brighteners, perfumes, anti-dusting agents, enzymes, dispersants, dye transfer inhibitors, pigments, odor masking agents, or a combination thereof.

Surfactants of particular interest are anionic and nonionic surfactants used in concentrations from 0 to 2%, such as, but not limited to, FMC HRS™, polyoxylene ($C_{20}$ to $C_{80}$) sorbitan monooleates, alklyl long chain fatty acid ($C_5$ to $C_{20}$) metallic esters and alcohols; and alkylbenzenesulfonic acids and alcohols and/or their metallic ester salts having alkyl groups ranging from $C_2$ to $C_{20}$.

The invention is preferably formulated as a liquid composition, preferably an aqueous composition. The pH of the composition is preferably between 2-5 pH and may be maintained by adjustment with PAA, citric, or acetic acid or mixture of these acids. The PAA and adjuvant solution can be combined into one solution to which can be added a foaming agent, (i.e., FMC HRS™) at a rate of 2-10 liquid ounces per gallon of sanitizer solution and applied by means of devices and equipment known in the art. The invention may also be combined by means of a two-part spray system (PAA solution and adjuvant) to surfaces. PAA formulations are generally marketed as concentrates. The adjuvant of the invention can therefore be provided as an additive formulation. An illustrative formulation is a 10× concentration consisting of approximately 79% acetic acid, 14.2% water, 5.6% citric acid, and 1.2% Na salicylate. Additionally, the adjuvant of the invention may be provided as a dry powder having a ratio of citric acid to Na salicylate of 4.67:1 by weight.

Target Organisms:

The compositions of the invention are effectively used to sanitize or disinfect food and surfaces where microbial populations are the result of contamination by fecal matter or digestive tract content. Additionally, contamination by other microbial vectors is also effectively reduced or eliminated by applying the disclosed compositions. The invention is effective in combating a variety of microorganisms including, but not limited to:

| | |
|---|---|
| Gram positive bacteria | *Bacillus*, *Listeria*, *Staphylococcus*, *Streptococcus*, *Enterococcus*, and *Clostridium*. |
| Gram negative bacteria | *Escherichia*, *Salmonella*, *Pseudomonas*, *Moraxella*, *Heliobactor*, *Stenotrophomonas*, *Acetobactoer*, and *Bdellovibrio*. |
| Viruses | Avian viral types and influenza species |
| Fungi & Molds | *Penicillium* spp., *Geotrichum* spp., *Aspergillus* spp. |
| Yeasts | *Candida* spp., *Rhyzopus* spp., *Mucor*. |

The microorganisms used in developing this invention and in the examples below were obtained from the American Type Culture Collection (ATCC), Manassas, Va. 20108 or from Remel Microbiology Products, Lenexa, Kans., 66215 USA. Specific organisms studied with use of the AOAC Use-Dilution Method in the development of this invention were *Pseudomonas aeruginosa* (ATCC 15442), *Staphylococcus aureus* (ATCC 6538), *Salmonella choleraesuis* (ATCC 10708). Specific organisms studied for germicidal and detergent sanitizing action were *Escherichia coli* (ATCC 11229) and *Staphylococcus aureus* (ATCC 6538). Additionally studied in a moist environment in contact with fruit juice were species *C. parapsilosis* and *M. plumbeus*.

Types of Environments and Methods of Application:

The compositions of this invention are suitable for use in a wide variety of environments including circulation cleaning in place (CIP) and industrial sanitizing of equipment such as tanks pipelines, evaporators, fillers, pasteurizers, aseptic equipment, and for sanitizing previously cleaned, hard, porous and non-porous food contact surfaces of equipment in, for example, 1) dairies, wineries, breweries, and beverage plants, 2) meat and poultry processing and packing plants, 3) milk and dairy products processing and packaging plants, 4) seafood and produce processing and packaging plants, 5) food processing and packing plants, 6) egg processing and packing equipment surfaces, and 7) eating establishments. Microbial populations are reduced in continuous online applications or in discontinuous batch applications. The composition may be recovered for reprocessing/reapplication to poultry, meat, seafood, plant materials, and to surfaces.

Direct Contact with Food:

The compositions are useful for treating and intervening with microbial vectors as applied to any kind of poultry (i.e., chicken, turkey, duck, ostrich, emu, quail, partridge, squab, guinea fowl, pheasant, goose, and game hens), red meat (i.e., beef, buffalo, pork, veal, lam, and mutton), and seafood (fish and shellfish). Also, to animal, poultry, or seafood carcasses that have been subjected to stunning, bleeding, scalding, picking, singeing, or a combination thereof. Also, to meat and poultry that have been subjected to beheading, removing feet, neck-cropping, portioning, or a combination thereof. Also, to a whole carcass or individual parts of carcasses (parts) or one or more dismembered parts of a carcass. Also, to a carcasses (parts) that has/have been subjected to portioning, or to any portion or combination thereof that has been subjected to deboning.

The composition may also be applied to plant material (i.e., leaf, stalk, flower, fruit, vegetable, or portion thereof) for treating and intervening with the growth of microbial vectors.

Treatment of food material may be by any suitable means including, for example, dip, spray nozzle or electrostatic spray system. Additionally, in poultry processing it may be applied within a de-feathering picker, inside-outside bird washing, dress rinsing, spray rinsing, or a combination thereof. Application may further include treating food material with the composition and then exposing the treated food material to activated light. Activated light is defined as ultraviolet light, infrared light, visible light or a combination thereof. Treatment may alternatively be by air chilling. The composition may be applied at temperatures between about 0° C. and 100° C. for use of the composition with direct food contact.

Surface Applications:

Surfaces prone to contamination with microorganisms can be found in many industries. Automated, clean-in-place (CIP) systems are widely used in food and beverage plants throughout product reception, storage, and process areas. This practice has expanded the need for cold terminal sanitation of stainless steel storage silos and process tanks, particularly in dairies and breweries. The advantages of CIP systems to the processors are savings in personnel, energy, and chemical costs by prevention of misuse by employees. Potential difficulties encountered using CIP systems are effective removal of soils, uniform surface contact by cleaners and sanitizers, problems with foam, and cross contamination problems associated with the practice of processing multiple product lines.

In these applications, the composition is applied to solid surfaces for the control of microbiological organisms. Surfaces may be porous or non-porous. One method for applying the composition is by a dual feed pump dosing system using ratio control or other means to proportionately meter the active formulations into a common stream of water or other appropriate carrier for the peracetic acid and additives (salicylic and citric) to be applied onto surfaces such as, but not limited to, any and all food processing equipment, bottle washing systems (including but not limited to such systems for glass, HDPE, MDPE, LLDPE and PET, and PLA), food contact surfaces, or other non-food processing surfaces. Application to surfaces may be accomplished, with or without foam additive, as treatments for food contact surfaces in restaurants, hospitals, and other industrial and institutional areas requiring sanitization and disinfection. Additionally, application may be accomplished, with or without foaming additives, as treatments for non-food contact surfaces such as, but not limited to, locker rooms, shower facilities, toilets, rest rooms, and counter tops.

The invention is exemplified in the following examples. The examples are illustrative of the invention and not intended to be limiting.

EXAMPLES

Methods and Materials

"RB" refers to a mixture of 0.2% sodium salicylate (Mallinckrodt powder) and 0.5% citric acid (Sigma anhydrous crystal), each ingredient added separately as a solid.

P-077-22 is a solution comprised of 81% acetic acid, 8% water, 7.6% citric acid, and 3.0% salicylic acid. P-077-23 is a solution comprised of 79% acetic acid, 14.2% water, 5.6% citric acid, and 1.2% sodium salicylate. In all studies, the "P" solutions were added such that the final test solutions contained 0.5% citric acid. For P-077-22 the actual weight of "as is" solution used was 6.58%; and for P-077-23 the weight was 8.93%.

The acronym "POESM" refers to Tween 80 (polyoxyethylene 20 sorbitan monooleate). The acronym "DDBSA" refers to dodecylbenzenesulfonic acid, and "SLS" refers to sodium lauryl sulfate.

Use of oxidative lysing agents such as peracetic acid in aqueous solution at concentration(s) ranging from 400-660 ppm provided only moderate kill rates with log reductions of 4-5.5. However, use of peracetic acid at the same concentrations with the addition of the adjuvant herein described produced improved kill rates up to complete destruction of the species with log reductions of 6 or recovery rates of 0. Additional testing of peracetic acid at nominal rates of 0-200 ppm with and without the adjuvant clearly demonstrated that complete control against *C. albicans* was achieved only when both PAA and the adjuvant were deployed together.

Additional testing to prove control as a disinfectant and not have interference between the adjuvant with the peracetic acid (VigorOx® LS&D, FMC, USA) was demonstrated through a $3^{rd}$ party laboratory with complete control of the tested organisms and met U.S. EPA disinfection claims. Similar testing also demonstrated similar performance with a third party laboratory as a sanitizer for pre-cleaned, non-porous food contact surfaces meeting the U.S. EPA definition for sanitizer performance.

The method of deployment consisted of peracetic acid in a water carrier fluid to which has been added the adjuvant herein described and then applied to the surface(s) to be treated and held for a specific period of time determined by field application testing. All the components were compounded into a single homogeneous mixture.

In the examples, the combination of 0.2% sodium salicylate and 0.5% citric acid added as solids (RB) or as dissolved in acetic acid (P-077-23) significantly enhanced the efficacy of VigorOx® versus microbes with thick cell walls such as Gram-positive bacteria, yeasts, and molds. This increase in biocidal effectiveness is most likely due to cell wall damage/changes caused by the adjuvants, allowing further penetration by peracetic acid. Since VigorOx® is highly/totally effective against thinner-walled Gram-negative bacteria, the addition of adjuvants results in no/little difference in efficacy against these microbes.

In parallel tests, the P-077-22 formulation containing salicylic acid achieved practically identical reductions as the sodium salicylate-containing version against all microbes except the spoilage mold *Rhizopus oryzae*. Thus, studies conducted to date indicate that P-077-23 is the more effective formulation; however, it should be noted that only one study versus *Rhizopus* indicated that P-077-22 was inferior. (See Example 4.)

Disinfecting Test Method:

Laboratory Procedures

Preparation of Challenge Inoculi for IsoGrid and Suspension Efficacy Testing

For bacterial studies, test microbes obtained from ATCC or Remel were first streaked on nutrient agar plates to confirm purity. Some of the plate growth was then transferred to nutrient broth and stirred at ~37° C. for ~24 hrs. or until growth reaches a level of 8 $\log_{10}$ colony forming units (CFU)/ml. This broth was then serially diluted in nutrient broth with 5% calf serum (added as an organic burden) to prepare a ~6 $\log_{10}$ CFU/ml suspension for the inoculation of test filters and a ~2 $\log_{10}$ CFU/ml suspension for the inoculation of positive control filters.

For yeast studies, test microbes obtained from ATCC or Remel were streaked on appropriate agar to confirm purity and then spread over the entire surface of several agar plates. After an incubation period of sufficient length to yield heavy growth, the surface of the agar was gently scraped with an inoculating loop to transfer the growth to a tube of sterile Butterfield's buffer (generally one plate of growth in ~100 ml buffer). The concentration (CFU/ml) of the resulting suspension was determined by using a hemacytometer or inoculating agar plates or IsoGrid filters. The mixture was refrigerated and was usable for several weeks after preparation. On the day of testing, the suspension was serially diluted in Butterfield's phosphate buffer to a level of ~5-6 $\log_{10}$ CFU/ml for the inoculation of test filters and a ~2 $\log_{10}$ CFU/ml suspension for the inoculation of positive control filters.

For mold studies, test microbes obtained from ATCC or Remel were streaked on appropriate agar to confirm purity and then spread over the entire surface of several agar plates. After an incubation period of sufficient length to yield confluent growth and sporulation, the plates were flooded with 6-10 ml sterile Butterfield's buffer. A hockey stick plate spreader was used to gently scrape the surface of the agar to loosen conidia and hyphae. The suspension on the agar was then poured off and filtered through sterile gauze in a sterile Buchner funnel with receiving flask. The concentration (CFU/ml) of the resulting conidial filtrate was determined by using a hemacytometer or inoculating agar plates or IsoGrid filters. The mixture was refrigerated and was usable for several weeks after preparation. On the day of testing, the suspension was serially diluted in Butterfield's phosphate buffer to a level of ~5-6 $\log_{10}$ CFU/ml for the inoculation of test filters and a ~2 $\log_{10}$ CFU/ml suspension for the inoculation of positive control filters.

Preparation of Test Solutions

Peracetic acid (PAA) solutions were prepared by diluting 5% or 15% VigorOx® with "Milli-Q" water in a passivated amber bottle to obtain the target concentration. The concentration was then confirmed by titration on an autotitrator.

Mixtures of PAA and amounts of adjuvants </=1 g/100 g mixture were prepared by weighing the adjuvant directly into a passivated amber bottle and adding previously prepared peracetic acid to reach the desired total weight. The PAA content was determined by titrating with a test PAA kit #7191 (LaMotte Company, Chestertown, Md. 21620 USA).

Mixtures of PAA and amounts of adjuvants >/=1 g/100 g mixture were prepared by weighing the adjuvant and the peracetic acid separately into a passivated amber bottle and using Milli-Q water to reach the desired total weight. The PAA content was determined by titrating with a test PAA kit #7191 (LaMotte Company, Chestertown, Md. 21620 USA).

IsoGrid Efficacy Testing

Using aseptic technique, IsoGrid filters (enough to run each test solution/condition in triplicate), were clamped in filter funnel units and each inoculated with a target of ~100,000 to one million CFU. This was accomplished by first adding ~12 ml sterile Butterfield's buffer to the funnel followed by 1 ml of ~$10^5$-$10^6$ CFU/ml inoculum suspension, and then removing all fluid under vacuum. Positive controls were similarly prepared by adding 1 ml of a ~$10^2$ CFU/ml suspension. Afterwards, filters are transferred to empty sterile Petri dishes and dried with dish lids cracked open for ~15 min. in a biosafety cabinet. For treatment, each dried test filter is mounted in a filter funnel unit to which 15 ml of test biocide solution is then added. After the desired treatment time, the biocide is neutralized by the addition of 50 ml of Letheen broth with 0.5% sodium thiosulfate; all fluid removed under vacuum, and the filter transferred to an agar plate. The plates are enumerated after an appropriate incubation period.

Suspension Efficacy Testing

For this type of study, one ml of challenge inoculum (~6-7 $\log_{10}$ CFU/ml) is mixed with nine ml of biocide in a sterile tube at Time 0. At precisely timed intervals, one ml aliquots of this reaction mixture are transferred to sterile tubes containing 9 ml neutralizing solution (Letheen broth with 0.5% sodium thiosulfate). Afterwards, the contents of each neutralizer tube are poured onto an IsoGrid filter mounted in a filter funnel unit (as used in the IsoGrid testing described above). Each tube is twice rinsed with sterile Butterfield's buffer and the rinsate added to the funnel unit before all fluid is removed under vacuum. Positive controls are prepared by serially diluting the ~6-7 $\log_{10}$ CFU/ml inoculum suspension in Butterfield's buffer to make a ~2 $\log_{10}$ CFU/ml suspension. One ml of this suspension is then used to inoculate triplicate IsoGrid filters. All filters are transferred to agar plates, incubated, and enumerated.

The following tables list the reductions achieved by test biocides against several types of microbes in both IsoGrid and suspension studies.

Example 1

VigorOx® at low concentrations with adjuvant showed significant enhanced activity against these spoilage bacterial organisms. All tests were run in triplicate. Tests were conducted at room temperature and for 30 sec.

TABLE 1.1

| Biocide Treatment | Species Challenge | Avg. $\text{LOG}_{10}$ Recovery | Avg. $\text{LOG}_{10}$ Reduction [−] |
|---|---|---|---|
| Control (FMC table 1) | E. coli | 6.4206 | — |
| 85 ppm PAA VigorOx ® (5%) | E. coli | 0.0001 | −6.4205 |
| 85 ppm PAA VigorOx ® (5%) + RB | E. coli | 0 | −6.4206 |
| Control | P. aeruginosa | 7.5714 | — |
| 85 ppm PAA VigorOx ® (5%) | P. aeruginosa | 0.9736 | −6.5978 |
| 85 ppm PAA VigorOx ® (5%) + Adjuvant (RB, P-077-22 and P-077-23 all got complete kills) Table 4 FMC data | P. aeruginosa | 0 | −7.5714 |
| Control (FMC Table 5) | S. aureus* | 5.9403 | — |
| 85 ppm PAA VigorOx ® (5%) | S. aureus* | 4.5858 | −1.3544 |
| 85 ppm PAA VigorOx ® (5%) + P-077-23 | S. aureus* | 0.2596 | −5.6807 |

*S. aureus past expiration date.

Example 2

*Candida parapsilosis* vs. VigorOx® and VigorOx® with Adjuvant.

The VigorOx® with adjuvant showed significant enhanced activity against this spoilage yeast organism. Testing at room temperature showed complete kill at the three time intervals and no residual for future colonization.

TABLE 2.1

| Biocide | Candida parapsilosis Challenge | Count (MPN) 30 sec. | Count (MPN) 45 sec. | Count (MPN) 60 sec. |
|---|---|---|---|---|
| 440 ppm PAA 15% VigorOx ® | 1.69 × 107 | TNTC | TNTC | TNTC |
| 440 ppm PAA VigorOx ® with Adjuvant | 1.69 × 107 | 0 | 0 | 0 |

Example 3

Modified Suspension Efficacy Study vs. *Mucor plumbeus*

*Mucor plumbeus* is a problematic spoilage yeast. 1 ml $1.1 \times 10^7$ cfu/ml *Mucor plumbeus* suspension was added to 9 ml of prepared biocide at time 0.1 ml of reaction mixture was transferred to a tube containing 9 ml Letheen plus 0.5% sodium thiosulfate at 30 sec., 45 sec., and 60 sec. Each tube of neutralized mixture was used to inoculate an IsoGrid filter. Tube was then rinsed with Butterfield's buffer twice and the rinsate poured back into the IsoGrid funnel and removed under vacuum.

Filters were plated on malt agar and incubated at room temperature for 5 days. Inoculum suspension was serially diluted in Butterfield's buffer and the $10^{-6}$ dilution plated on triplicate IsoGrid filters.

TABLE 3.1

Modified Suspension Efficacy Study vs. *Mucor plumbeus*

| Biocide | Mucor Challenge | Count (MPN) 30 sec. | Count (MPN) 45 sec. | Count (MPN) 60 sec. |
|---|---|---|---|---|
| 440 PAA 5% VigorOx ® | $1.1 \times 10^7$ | TNTC | TNTC | TNTC |
| 440 PAA 5% VigorOx ® + Adjunct test A | $1.1 \times 10^7$ | 0 | 0 | 0 |
| 440 PAA 5% VigorOx ® + Adjunct test B | $1.1 \times 10^7$ | 0 | 0 | 0 |

TNTC = too numerous to count

Example 4 *R. oryzae* Challenge with VigorOx® & VigorOx® with Adjuvant 1 ml $2.69 \times 10^7$ cfu/ml *Rhizopus oryzae* mold suspension was added to 9 ml of prepared biocide at time 0.1 ml of reaction mixture was transferred to a tube containing 9 ml Letheen plus 0.5% sodium thiosulfate at 30 sec., 45 sec., and 60 sec. Each tube of neutralized mixture was used to inoculate an IsoGrid filter. The tube was then rinsed with Butterfield's buffer twice and the rinsate poured back into the IsoGrid funnel and removed under vacuum. Filters were plated on malt agar and incubated at room temperature for 1 day. Inoculum suspension was serially diluted in Butterfield's buffer and the 10-5 dilution plated on triplicate IsoGrid filters.

TABLE 4.1

*R. oryzae* Challenge with VigorOx ® & VigorOx ® with Adjuvant

| Biocide | Rhizopus Challenge | Count (MPN) 30 sec. | Count (MPN) 45 sec. | Count (MPN) 60 sec. |
|---|---|---|---|---|
| 440 ppm PAA 5% VigorOx ® | $2.69 \times 10^7$ | TNTC | TNTC | TNTC |
| 440 ppm PAA VigorOx ® with Adjuvant | $2.69 \times 10^7$ | 0 | 0 | 0 |

TNTC = too numerous to count

What is claimed is:

1. An aqueous composition comprising,
   a. an aqueous peracetic acid solution; and
   b. an adjuvant comprising (i) salicylic acid or a salt thereof and (ii) citric acid or a salt thereof wherein the salicylic acid or salt thereof and citric acid or salt thereof are in proportionate weight ratios ranging from 1:5 to 1:1 respectively, in a solution matrix of 70-90% glacial acetic acid and 5-30% water.

2. The composition of claim 1 wherein the salicylic acid and citric acid or their respective salts are dissolved to their solubility limits.

3. The composition of claim 2 further comprising one or more stabilizing agents, wetting agents, hydrotopes, thickeners, foaming agents, acidifiers, pigments, dyes, surfactants, or combinations thereof.

4. The composition of claim 3 wherein the surfactant consists of one or more anionic or nonionic surfactants in concentrations up to 2% selected from the group consisting of $C_{20}$ to $C_{80}$ polyoxylene sorbitan monooleates, $C_5$ to $C_{20}$ alkyl long chain fatty acid metallic esters and alcohols; and alkylbenzenesulfonic acids and alcohols and/or their metallic ester salts having $C_2$ to $C_{20}$ alkyl groups.

5. The composition of claim 1 wherein the salicylic acid or salt thereof is sodium salicylate and the citric acid or salt thereof is citric acid.

6. A kit comprising
   a. an aqueous peracetic acid solution; and
   b. an adjuvant comprising (i) salicylic acid or a salt thereof and (ii) citric acid or a salt thereof wherein the salicylic acid or salt thereof and citric acid or salt thereof are in proportionate weight ratios ranging from 1:5 to 1:1 respectively, in a solution matrix of 70-90% glacial acetic acid and 5-30% water.

7. A method of reducing microbial contamination comprising applying the aqueous composition of claim 1 to a surface in an amount and for a time sufficient to reduce the microbial contamination.

8. The method of claim 7 wherein the surface is meat, poultry, seafood, or a portion thereof.

9. The method of claim 7, wherein the surface is a plant material selected from the group consisting of a leaf or portion thereof, a stalk or portion thereof, a flower or portion thereof, a fruit or portion thereof, and a vegetable or portion thereof.

10. The method of claim 7 wherein the surface is a non-food contact surface.

11. The method of claim 7 further comprising recovering the applied composition and reprocessing the recovered composition to yield a recycled anti-microbial composition.

12. The method of claim 7 wherein the peracetic acid is present at in the aqueous composition at a concentrations ranging up to 1%.

13. The method of claim 7 wherein the salicylic acid or salt thereof is present at up to 20000 ppm.

14. The method of claim 7 wherein the citric acid is present up to 20000 ppm.

15. The method of claim 7 wherein the aqueous composition has a pH value between 1 and 4.5.

16. The aqueous composition of claim 1, wherein the peracetic acid is present in the aqueous composition at concentrations ranging up to 1%.

\* \* \* \* \*